[54] 7-AMINO-BENZOCYCLOHEPTENES

[75] Inventors: Lucien Nedelec, Le Raincy; André Pierdet, Noisy-le-Sec; Claude Dumont, Nogent-sur-Marne; Marie-Helene Kannengiesser, Paris, all of France

[73] Assignee: Roussel Uclaf, Paris, France

[21] Appl. No.: 708,749

[22] Filed: Jul. 26, 1976

[30] Foreign Application Priority Data

Jul. 28, 1975 France .................... 75 23499

[51] Int. Cl.$^2$ ................ A61K 31/135; C07C 87/45
[52] U.S. Cl. ............................. 424/330; 544/398; 544/403; 544/401; 260/293.72; 260/326.81; 260/570.5 R; 260/570.5 C; 424/248.58; 424/250; 424/248.4; 424/267; 424/274; 544/174; 544/178
[58] Field of Search ........... 260/268 BC, 570.5 R, 260/326.81; 424/250, 330

[56] References Cited

U.S. PATENT DOCUMENTS 3,751,420  8/1973  Hauck et al. ............... 260/570.5 R
3,836,534  9/1974  Drukker et al. ............ 260/570.5 R

*Primary Examiner*—Paul M. Coughlan, Jr.
*Attorney, Agent, or Firm*—Hammond & Littell

[57] ABSTRACT

Novel 7-amino-benzocycloheptenes of the formula

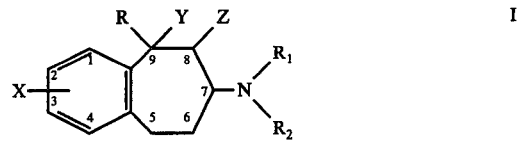

wherein X is selected from the group consisting of hydrogen, chlorine, bromine and iodine in the 2- or 4-position when a halogen, Y and Z are hydrogen or together form a double bond, R is selected from the group consisting of hydrogen, alkyl of 1 to 5 carbon atoms and phenyl optionally substituted with fluorine, chlorine, methyl or methoxy, $R_1$ is selected from the group consisting of hydrogen, alkyl of 1 to 5 carbon atoms and alkenyl of 2 to 5 carbon atoms and $R_2$ is selected from the group consisting of alkyl of 1 to 5 carbon atoms and alkenyl of 2 to 5 carbon atoms and $R_1$ and $R_2$ taken together with the nitrogen atom to which they are attached form a saturated heterocycle of 4 to 6 carbon atoms and optionally containing another hetero-atom and optionally substituted with an alkyl of 1 to 5 carbon atoms and their non-toxic, pharmaceutically acceptable acid addition salts having antidepressive activity and their preparation and novel intermediates.

19 Claims, No Drawings

7-AMINO-BENZOCYCLOHEPTENES

OBJECTS OF THE INVENTION

It is an object of the invention to provide the novel products of formula I and their non-toxic, pharmaceutically acceptable acid addition salts.

It is a further object of the invention to provide a novel process for the preparation of the compounds of formula I and novel intermediates produced thereby.

It is another object of the invention to provide novel anti-depressive compositions and to a novel method of relieving depression in warm-blooded animals.

These and other objects and advantages of the invention will become obvious from the following detailed description.

THE INVENTION

The novel products of the invention are selected from the group consisting of 7-amino-benzocycloheptenes of the formula

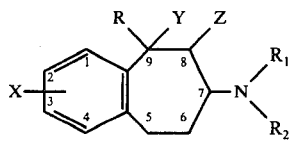

wherein X is selected from the group consisting of hydrogen, chlorine, bromine and iodine in the 2- or 4-position when a halogen, Y and Z are hydrogen or together form a double bond, R is selected from the group consisting of hydrogen, alkyl of 1 to 5 carbon atoms and phenyl optionally substituted with fluorine, chlorine, methyl or methoxy, $R_1$ is selected from the group consisting of hydrogen, alkyl of 1 to 5 carbon atoms and alkenyl of 2 to 5 carbon atoms and $R_2$ is selected from the group consisting of alkyl of 1 to 5 carbon atoms and alkenyl of 2 to 5 carbon atoms and $R_1$ and $R_2$ taken together with the nitrogen atom to which they are attached form a saturated heterocycle of 4 to 6 carbon atoms and optionally containing another hetero-atom and optionally substituted with an alkyl of 1 to 5 carbon atoms and their non-toxic, pharmaceutically acceptable acid addition salts.

Examples of alkyl of 1 to 5 carbon atoms are methyl, ethyl, propyl, isopropyl, butyl, isobutyl or pentyl and alkenyl of 2 to 5 carbon atoms may be vinyl, allyl, buten-2-yl or penten-2-yl. Saturated heterocycles of 2 to 4 carbon atoms and optionally containing a second heteroatom and/or substituted with alkyl of 1 to 5 carbon atoms may be pyrrolidino, piperidino, morpholino, piperazinyl, N-methyl-piperazinyl, N-ethyl-piperazinyl, N-propyl-piperazinyl or N-butylpiperazinyl, X is preferably bromo or chloro.

Among the preferred compounds of formula I are those where X is hydrogen or chloro, R is hydrogen, methyl or phenyl, $R_1$ is hydrogen, methyl, ethyl, propyl, or allyl, $R_2$ is methyl, ethyl, propyl or allyl or $R_1$ and $R_2$ together with the nitrogen atom form pyrrolidino, piperidino, morpholino, piperazinyl or N-methylpiperazinyl. In the more preferred compounds of formula I, R is hydrogen or phenyl, $R_1$ is hydrogen, methyl, ethyl or allyl, $R_2$ is methyl, ethyl or allyl or $R_1$ and $R_2$ together with the nitrogen atom form pyrrolidino or N-methyl-piperazinyl.

In another group of preferred compounds of formula I, $R_1$ is hydrogen or methyl and $R_2$ is methyl, ethyl or allyl.

In the case of the compounds of formula I wherein R is alkyl of 1 to 5 carbon atoms or phenyl optionally substituted with fluorine, chlorine, methyl or methoxy and Y and Z are hydrogen, the compounds occur in the form of two isomers designated as isomers A and B which may be separated into individual isomers by known methods.

Examples of suitable acids for the preparation of the non-toxic, pharmaceutically acceptable acid addition salts are inorganic acids such as hydrochloric acid, hydrobromic acid, hydroiodic acid, nitric acid, sulfuric acid or phosphoric acid or organic acids such as acetic acid, formic acid, benzoic acid, maleic acid, fumaric acid, succinic acid, tartaric acid, citric acid, oxalic acid, glyoxylic acid, aspartic acid, alkane sulfonic acids such as methane or ethane sulfonic acids, aryl sulfonic acids such as benzene sulfonic acid or p-toluene sulfonic acid or arylcarboxylic acids.

The novel process of the invention for the preparation of the compounds of formula I comprises deshydrating a compound of the formula

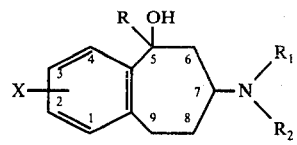

wherein X, R, $R_1$ and $R_2$ have the above definition to obtain a compound of the formula

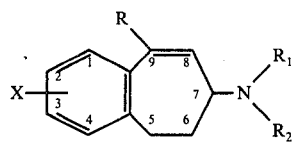

which may be isolated or salified or reduced to obtain a compound of the formula

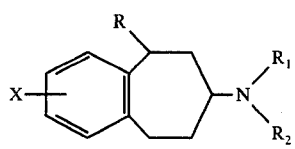

which may be isolated per se or salified.

The preferred mode of the process effects the deshydration at reflux temperatures with a strong acid such as hydrochloric acid or sulfuric acid or with potassium bisulfate or by heating in hexametapol. The reduction of the compound of formula Ia is effected with gaseous hydrogen in the presence of a catalyst such as palladium.

In a variation of the process of the invention to produce a compound of formula Ib, a compound of formula II is energetically reduced to obtain the compound of formula Ib. The said reduction may be advantageously effected with sodium in liquid ammonia and in the presence of a low molecular weight alkanol such as methanol.

The acid addition salts of the compounds of formula I may be prepared by reacting the free base with an approximately stoichiometric amount of the said acid. The base may or may not be isolated before reaction with the acid.

The compounds of formula II used as the starting materials for the process may be prepared by reacting a compound of the formula

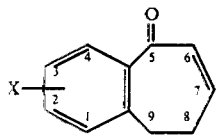
III wherein X has the above definition with an amine of the formula

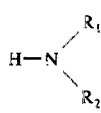
IV to obtain a compound of the formula

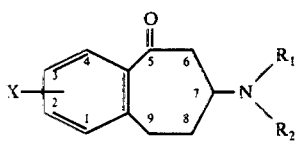
V and either the compound of formula V is reacted with a compound of the formula

M—R     VI wherein M is lithium or —MgHal and Hal is chlorine or bromine and R is defined as above except that it is not hydrogen to obtain a compound of the formula

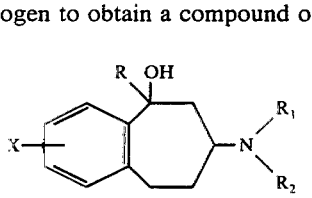
II wherein X, $R_1$ and $R_2$ have the above definition and R is as defined above except it is not hydrogen or the compound of formula V may be reduced to form a compound of the formula

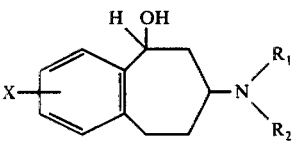
IIa

In a preferred process for the preparation of the compounds of formula II, the reaction of compounds of formula III and IV is effected at room temperature in a low molecular weight alkanol such as ethanol and the reaction with the organometallic compound of formula IV and the compound of formula V is effected in an anhydrous ether such as ethyl ether or tetrahydrofuran. The reduction of the compound of formula V is effected with sodium borohydride in the presence of a low molecular weight alkanol such as ethanol or with lithium aluminum hydride in an organic solvent such as tetrahydrofuran.

The process for the preparation of the compounds of formula I wherein $R_1$ and $R_2$ are idential or different and are alkyl of 1 to 5 carbon atoms or alkenyl of 2 to 5 carbon atoms comprises reacting a compound of the formula

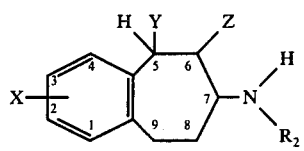
Ic with a halide of the formula

Hal—$R_1$     VIII wherein Hal is chlorine, bromine or iodine and $R_1$ is defined as above to obtain the corresponding compound of formula I.

The compounds of formula I wherein $R_1$ is methyl and $R_2$ is alkyl of 1 to 5 carbon atoms and X, Y, Z and R are defined as above may be prepared by reacting a compound of the formula

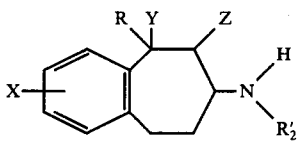
Id wherein $R_2'$ is alkyl of 1 to 5 carbon atoms with formaldehyde and sodium cyanoborohydride.

The anti-depressive compositions of the invention are comprised of an effective amount of at least one compound of formula I and their non-toxic, pharmaceutically acceptable acid addition salts and an inert pharmaceutical carrier. The compositions may be in the form of tablets, dragees, gelules, granules, suppositories, and injectable solutions or suspensions prepared in the usual way.

Examples of suitable pharmaceutical carriers or excipients are talc, arabic gum, lactose, starch, magnesium stearate, cacao butter, aqueous or non-aqueous vehicles, fatty bodies of animal or vegetable origin, paraffinic derivatives, glycols, preservatives and diverse wetting agents, dispersants and emulsifiers.

The compositions of the invention are useful for the treatment of depression, melancholy, maniac-depressive psychoses, reactionnal depressions, depressions due to exhaustion, nevrotic depressions and in the treatment of symptoms of Parkinson disease.

Among the preferred compositions are those wherein in the compounds of formula I, X is hydrogen or chlorine, R is hydrogen, methyl or phenyl, $R_1$ is hydrogen, methyl, ethyl, propyl or allyl, $R_2$ is methyl, ethyl, propyl or allyl or $R_1$ and $R_2$ together with the nitrogen atom form pyrrolidino, piperidino, morpholino, piperazinyl or N-methyl-piperazinyl. In the more preferred compounds of formula I, R is hydrogen or phenyl, $R_1$ is hydrogen, methyl, ethyl or allyl, $R_2$ is methyl, ethyl or allyl or $R_1$ and $R_2$ together with the nitrogen atom form pyrrolidino or N-methyl-piperazinyl.

In another group of preferred compounds of formula I, $R_1$ is hydrogen or methyl and $R_2$ is methyl, ethyl or allyl.

Among specific preferred compounds of formula I are 7-dimethylamino-6,7-dihydro [5H] benzocycloheptene, the A and B isomers of 7-dimethylamino-5-phenyl-6,7,8,9-tetrahydro [5H] benzocycloheptene, 7-methylamino-6,7,-dihydro [5H] benzocycloheptene and 2-chloro-7-methylamino-6,7-dihydro [5H] benzocycloheptene and their non-toxic, pharmaceutically acceptable acid addition salts.

The novel method of the invention for treating depressive states in warm-blooded animals, including humans, comprises administering to warm-blooded animals an anti-depressive effective amount of at least one compound of formula I and its non-toxic, pharmaceutically acceptable acid addition salts. The compounds may be administered orally, rectally or parenterally and the usual effective dose is 0.2 to 6 mg/kg depending on the product and the method of administration.

The novel intermediate products of the invention are those of formula II and formula V. Among the preferred compounds of formula II are 7-dimethylamino-5-hydroxy-6,7,8,9-tetrahydro [5H] benzocycloheptene, 7-dimethylamino-5-hydroxy-5-phenyl-6,7,8,9-tetrahydro [5H] benzocycloheptene, 7-methylamino-5-hydroxy-6,7,8,9-tetrahydro [5H] benzocycloheptene, 7-methylamino-5-hydroxy-5-phenyl-6,7,8,9-tetrahydro [5H] benzocycloheptene, 1-and 3-chloro-5-hydroxy-7-methylamino-6,7,8,9-tetrahydro [5H] benzocycloheptene, 7-ethylamino-5-hydroxy-6,7,8,9-tetrahydro [5H] benzocycloheptene hydrochloride, 1-(5-hydroxy-6,7,8,9-tetrahydro [5H] 7-benzocycloheptenyl)-4-methyl-piperazine and 7-(2-propenylamino)-5-hydroxy-6,7,8,9-tetrahydro [5H] benzocycloheptene.

Among the preferred compounds of formula V are 7-dimethylamino-6,7,8,9-tetrahydro [5H] benzocycloheptene-5-one, 7-methylamino-6,7,8,9-tetrahydro [5H] benzocycloheptene-5-one, 1- and 3-chloro-7-methylamino-6,7,8,9-tetrahydro [5H] benzocycloheptene-5-one, 7-ethylamino-6,7,8,9-tetrahydro [5H] benzocycloheptene-5-one hydrochloride, 1-(5-oxo-6,7,8,9-tetrahydro [5H]-7-benzocycloheptenyl)-4-methyl-piperazine and 7-(2-propenylamino)-6,7,8,9-tetrahydro [5H] benzocycloheptene-5-one hydrochloride.

The compounds of formula III wherein X is not hydrogen when they are not known, may be prepared by subjecting a compound of the formula

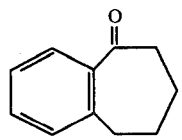

to a halogenation other than fluorination to obtain a compound of the formula

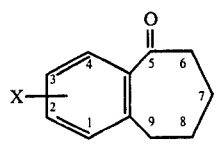

where X is chlorine, bromine or iodine in the 1 or 3 position of the phenyl ring and reacting the latter with cuprous bromide, bromine or a bromine complex such as pyridinium perbromide in an organic solvent to obtain a compound of the formula

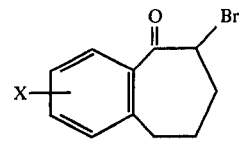

which is then dehydrobrominated with lithium bromide and lithium carbonate to obtain the corresponding compound of formula III.

In the following examples there are described several preferred embodiments to illustrate the invention. However, it should be understood that the invention is not intended to be limited to the specific embodiments.

EXAMPLE 1

7-dimethylamino-6,7-dihydro [5H] benzocycloheptene, hydrochloride

STEP A: 7-dimethylamino-5-oxo-6,7,8,9-tetrahydro [5H] benzocycloheptene 12.2 g of a 33% by weight solution of dimethylamino in benzene were added to a solution of 7 g of 5-oxo-8,9-dihydro [5H] benzocycloheptene in 70 ml of ethanol and the mixture was stirred at room temperature for 3 hours and was filtered. The filtrate was evaporated to dryness to obtain 8.7 g of raw 7-dimethylamino-5-oxo-6,7,8,9-tetrahydro [5H] benzocycloheptene which was used as is for the next step.

STEP B:
7-dimethylamino-5-hydroxy-6,7,8,9-tetrahydro [5H] benzocycloheptene

A solution of 8.7 g of sodium borohydride in 87 ml of water was added to a solution of 8.7 g of the product of Step A in 435 ml of ethanol and the mixture was stirred at 20° C for 1½ hours and was then poured into ice water. The mixture was saturated with sodium chloride and was extracted with ethyl acetate. The organic phase was washed with aqueous sodium chloride solution, was dried and evaporated to dryness to obtain 8 g of raw 7-dimethylamino-5-hydroxy-6,7,8,9-tetrahydro [5H] benzocycloheptene which was used as is for the next step.

STEP C: 7-dimethylamino-6,7-dihydro [5H] benzocycloheptene hydrochloride 16 ml of 18 N sulfuric acid were added to a refluxing mixture of 8 g of 7-dimethylamino-5-hydroxy-6,7,8,9-tetrahydro [5H] benzocycloheptene and 80 ml of dioxane and after one half hour of reflux, another 80 ml of dioxane were added thereto. The mixture was refluxed another 30 minutes and was then cooled. The pH was raised above 10 by addition of concentrated ammonium hydroxide and the mixture was saturated with sodium chloride and was extracted with ethyl acetate. The organic extracts were washed with aqueous sodium chloride and then were dried and evaporated to dryness. The residue was chromatographed over silica gel and was eluted with a 7-3-1 cyclohexane-ethyl acetate-triethylamine mixture to obtain 3.6 g of 7-dimethylamino-6,7-dihydro [5H] benzocycloheptene.

The said product was dissolved in ethyl ether and a ether solution saturated with hydrogen chloride was added thereto and the mixture was vacuum filtered. The recovered precipitate was crystallized from isopropanol to obtain 2.8 g of 7-dimethylamino-6,7-dihydro [5H] benzocycloheptene hydrochloride melting at 172° C.

| Analysis: $C_{13}H_{18}ClN$ | | | | |
|---|---|---|---|---|
| Calculated: | %C 69.78 | %H 8.10 | %N 6.25 | %Cl 15.84 |
| Found: | 70.0 | 8.2 | 6.3 | 15.8 |

EXAMPLE 2

7-dimethylamino-6,7,8,9-tetrahydro [5H] benzocycloheptene hydrochloride

A mixture of 11.2 g of 7-dimethylamino-6,7-dihydro [5H] benzocycloheptene, 800 ml of ethanol and 11.2 g carbon containing 10% of Pd (OH)$_2$ was held under a hydrogen atmosphere for 30 minutes and when the theoretical amount of hydrogen had been absorbed, the mixture was filtered. The filtrate was evaporated to dryness and the residue was chromatographed over silica gel. Elution with an 8-2-1 ethyl acetate-benzene-triethylamine mixture yielded 4.1 g of 7-dimethylamino-6,7,8,9-tetrahydro [5H] benzocycloheptene.

The said product was dissolved in ethyl ether and an ether solution saturated with hydrogen chloride was added thereto. The mixture was filtered and the recovered precipitate was crystallized from an ethyl acetate-methylene chloride mixture to obtain 4.3 g of 7-dimethylamino-6,7,8,9-tetrahydro [5H] benzocycloheptene hydrochloride melting at 210° C.

| Analysis: $C_{13}H_{20}ClN$ | | | | |
|---|---|---|---|---|
| Calculated: | %C 69.16 | %H 8.93 | %N 15.70 | %Cl 6.20 |
| Found: | 68.9 | 8.9 | 15.9 | 6.3 |

EXAMPLE 3

7-dimethylamino-9-phenyl-6,7-dihydro [5H] benzocycloheptene hydrochloride

STEP A:
7-dimethylamino-5ξ-phenyl-5ξ-hydroxy-6,7,8,9-tetrahydro [5H] benzocycloheptene A solution of 24.46 g of 7-dimethylamino-5-oxo-6,7,8,9-tetrahydro [5H] benzocycloheptene in 488 ml of ethyl ether was added over 75 minutes under a nitrogen atmosphee at 0° to 5° C to a solution of 1.2 M of phenyl lithium in ethyl ether and the mixture was stirred for 2 hours at 0° to 5° C. 120 ml of an aqueous saturated ammonium chloride solution and then 100 ml of water were slowly added thereto at 0° to 15° C and the mixture was decanted. The ether phase was washed with water and dried to obtain 29.4 g of raw 7-dimethylamino-5ξ-phenyl-5ξ-hydroxy6,7,8,9-tetrahydro [5H] benzocycloheptene which was used as is for the next step. The product was a mixture of the 2 isomers with substitution in the 5-position.

STEP B: 7-dimethylamino-9-phenyl-6,7-dihydro [5H] benzocycloheptene hydrochloride A mixture of 29.1 g of 7-dimethylamino-5-phenyl-5-hydroxy-6,7,8,9-tetrahydro [5H] benzocycloheptene and 290 ml of dioxane was refluxed under an inert gas and then 60 ml of 18 N sulfuric acid were added thereto. The mixture was stirred for 3 minutes and after cooling, was poured over ice. The pH was adjusted above 10 by addition of concentrated ammonium hydroxide and the mixture was saturated with sodium chloride and was extracted with ethyl acetate. The organic extracts were washed with aqueous sodium chloride solution, were dried and evaporated to dryness. The residue was chromatographed over silica gel and was eluted with a 10-1 benzene-triethylamine mixture to obtain 20.2 g of 7-dimethylamino-9-phenyl-6,7-dihydro [5H] benzocycloheptene.

4 g of the said product were dissolved in 600ml of ethyl ether and an ether solution saturated with hydrogen chloride was added thereto. The mixture was vacuum filtered and the recovered precipitate was crystallized from isopropanol to obtain 3.6 g of 7-dimethylamino-9-phenyl-6,7-dihydro [5H] benzocycloheptene hydrochloride melting at a temperature above 270° C.

| Analysis: $C_{19}H_{22}ClN$ | | | | |
|---|---|---|---|---|
| Calculated: | %C 76.1 | %H 7.39 | %Cl 11.82 | %N 4.66 |
| Found: | 76.2 | 7.4 | 11.6 | 4.8 |

EXAMPLE 4

7-dimethylamino-5-phenyl-6,7,8,9-tetrahydro [5H] benzocycloheptene hydrochloride 5 g of palladized carbon [10% Pd(OH)$_2$] were added to a solution of 5 g of 7-dimethylamino-9-phenyl-6,7-dihydro [5H] benzocycloheptene in 250 ml of ethanol and the mixture was stirred under a hydrogen atmosphere at 20° C until absorption ceased. The mixture was filtered and the filtrate was evaporated to dryness. The residue was chromatographed over silica gel and elution with a 9-1-1 cyclohexane-ethyl acetate-triethylamine mixture yielded 0.52 g of isomer A (equatorial 5-H) and 2.9 g of isomer B (axial 5-H) of 7-dimethylamino-5-phenyl-6,7,8,9-tetrahydro [5H] benzocycloheptene.

0.47 g of isomer A were dissolved in 50 ml of ethyl ether and an ether solution saturated with hydrogen chloride was added thereto. The mixture was vacuum filtered and the recovered precipitate was crystallized from a methylene chloride-ethyl acetate mixture to obtain 0.44 g of the hydrochloride of said isomer A melting at 166° C.

| Analysis: $C_{19}H_{24}ClN$ | | | | |
|---|---|---|---|---|
| Calculated: | %C 75.59 | %H 8.01 | %N 4.63 | %Cl 11.74 |
| Found: | 75.4 | 8.1 | 4.5 | 11.6 |

Using the same procedure, 2.8 g of isomer B were reacted to obtain 2.9 g of the hydrochloride of isomer B melting at 202° C.

| Analysis: $C_{19}H_{24}ClN$ | | | | |
|---|---|---|---|---|
| Calculated: | %C 75.59 | %H 8.01 | %N 4.63 | %Cl 11.74 |
| Found: | 75.8 | 8.1 | 4.6 | 11.9 |

EXAMPLE 5

7-dimethylamino-5-phenyl-6,7,8,9-tetrahydro [5H] benzocycloheptene hydrochloride 12.4 ml of ethanol and then a solution of 12 g of 7-dimethylamino-5ξ-phenyl-5ξ-hydroxy-6,7,8,9-tetrahydro [5H] benzocycloheptene in 200 ml of tetrahydrofuran were added to 600 ml of condensed ammonia and then 2.46 of sodium were added at −40° C. The mixture was stirred at −40° C for 20 minutes and the ammonia and tetrahydrofuran were evaporated. The residue was dissolved in ethyl acetate and the solution was washed with water, dried and evaporated to dryness. The residue was chromatographed over silica gel and eluted with a 9-1-1 cyclohexane-ethyl acetate-triethylamine mixture to obtain 3.2 g of isomer A (equatorial 5-H) and 6.5 g of isomer B (axial 5-H) of 7-dimethylamino-5-phenyl-6,7,8,9-tetrahydro [5H] benzocycloheptene.

3.2 g of isomer A were reacted by the procedure of Example 4 to obtain 2.9 g of the hydrochloride of isomer A melting at 166° C.

Analysis: $C_{19}H_{24}NCl$ (solvated with ethyl acetate)

| | | | | |
|---|---|---|---|---|
| Calculated: | %C 74.25 | %H 8.01 | %N 4.63 | %Cl 11.74 |
| Found: | 74.2 | 8.2 | 4.5 | 11.4 |

EXAMPLE 6

7-methylamino-6,7-dihydro [5H] benzocycloheptene hydrochloride

STEP A: 7-methylamino-5-oxo-6,7,8,9-tetrahydro [5H] benzocycloheptene

A solution of 22.7 g of monomethylamine in 160 ml of benzene was added to a solution of 40 g of 5-oxo-8,9-dihydro [5H] benzocycloheptene in 400 ml of ethanol and the mixture was stirred for 2 ½ hours and was evaporated to dryness to obtain 47.5 g of 7-methylamino-5-oxo-6,7,8,9-tetrahydro [5H] benzocycloheptene which was used as is for the next step.

STEP B: 7-methylamino-5-hydroxy-6,7,8,9-tetrahydro [5H] benzocycloheptene

A solution of 47.5g of sodium borohydride in 475 ml of water was slowly added to a solution of 47.5 g of the product of Step A in 2.4 liters of ethanol and the mixture was stirred for 2 ½ hours and then was concentrated to 500 ml. The mixture was poured into 2 liters of aqueous sodium chloride solution and the mixture was extracted with ethyl acetate. The organic phase was washed with aqueous sodium chloride solution, dried and evaporated to dryness to obtain 50 g of raw 7-methylamino-5-hydroxy-6,7,8,9-tetrahydro [5H] benzocycloheptene which was used as is for the next step.

STEP C: 7-methylamino-6,7-dihydro [5H] benzocycloheptene hydrochloride 50 ml of 18 N sulfuric acid were added over 30 minutes to a refluxing mixture of 50 g of 7-methylamino-5-hydroxy-6,7,8,9-tetrahydro [5H] benzocycloheptene and 500 ml of dioxane and the mixture was refluxed for an hour and then was cooled. The pH was adjusted to 10 with concentrated ammonium hydroxide solution and the mixture was saturated with ammonium sulfate and was extracted with ethyl acetate. The organic phase was washed with aqueous sodium chloride solution, dried and evaporated to dryness and the residue was chromatographed over silica gel. Elution with a 95-5-2 methylene chloride-methanol-triethylamine mixture yielded 22.8 g of 7-methylamino-6,7-dihydro [5H] benzocycloheptene.

The said product was dissolved in 50 ml of ethyl acetate and an ethyl acetate solution saturated with hydrogen chloride was added. The mixture was vacuum filtered and the product was crystallized from ethanol to obtain 18 g of 7-methylamino-6,7-dihydro [5H] benzocycloheptene hydrochloride melting at 215° C.

Analysis: $C_{12}H_{16}NCl$

| | | | | |
|---|---|---|---|---|
| Calculated: | %C 68.72 | %H 7.69 | %Cl 16.91 | %N 6.68 |
| Found: | 68.8 | 7.7 | 16.8 | 6.4 |

The said hydrochloride was treated with 2 N sodium hydroxide and then reacted with levorotatory dibenzoyltartaric acid. The mixture was filtered and the recovered precipitate was treated with sodium hydroxide and then hydrochloric acid for the hydrochloride of dextrorotatory 7-methylamino-6,7-dihydro [5H] benzocycloheptene melting at 213° C and having a specific rotation of $[\alpha]_D^{20} = + 135.5° \pm 2.5°$ (c = 0.9% in methanol).

The filtrate from the filtration step was treated with dextrorotatory dibenzoyl tartaric acid and the salt was treated as above to obtain the hydrochloride of levorotatory 7-methylamino-6,7-dihydro [5H] benzocycloheptene melting at 213° C and having a specific rotation $[\alpha]_D^{20} = 138.5 \pm 2.5$ (c = 0.9% in methanol).

EXAMPLE 7

7-methylamino-6,7,8,9-tetrahydro [5H] benzocycloheptene hydrochloride

A mixture of 3.4 g of 7-methylamino-6,7-dihydro [5H] benzocycloheptene, 200 ml of ethanol and 3.4 g of 10% palladized carbon was maintained under a hydrogen atmosphere until absorption ceased and was then filtered. The filtrate was evaporated to dryness under reduced pressure to obtain 2.9 g of 7-methylamino-6,7,8,9-tetrahydro [5H] benzocycloheptene. The said product was dissolved in 300 ml of ether and an ether solution saturated with hydrogen chloride was added. The mixture was filtered and the recovered precipitate was crystallized from an 8-2 ethyl acetate-methanol mixture to obtain 2.6 g of the hydrochloride of 7-methylamino-6,7,8,9-tetrahydro [5H] benzocycloheptene melting at 270° C.

Analysis: $C_{12}H_{18}NCl$

| | | | | |
|---|---|---|---|---|
| Calculated: | %C 68.07 | %H 8.57 | %Cl 16.74 | %N 6.62 |
| Found: | 67.9 | 8.5 | 16.7 | 6.6 |

EXAMPLE 8

7-methylamino-9-phenyl-6,7-dihydro [5H] benzocycloheptene hydrochloride

STEP A:
7-methylamino-5-phenyl-5-hydroxy-6,7,8,9-tetrahydro [5H] benzocycloheptene 440 ml of a toluene solution of 1.35 M of phenyl magnesium bromide [prepared from a mixture of 26.76 g of magnesium, 105 ml of bromobenzene, 600 ml of tetrahydrofuran and 600 ml of toluene from which the tetrahydrofuran was distilled while keeping the volume constant] were added to a solution of 10.8 g of 7-methylamino-5-oxo-6,7,8,9-tetrahydro [5H] benzocycloheptene in 200ml of toluene and the mixture was refluxed for 2 ½ hours under an inert atmosphere and was then cooled. 200 ml of an aqueous saturated ammonium chloride solution was slowly added thereto at a maximum temperature of 15° C and the mixture was filtered. The filtrate was extracted with ethyl acetate and the organic extracts were washed with water, dried and evaporated to dryness. The residue was chromatographed over silica gel and was eluted with a 9-1 benzene-ethyl acetate mixture, a 2-8-1 benzene-ethyl acetate-triethylamine mixture and a 95-5-10 chloroform-methanol-triethylamine mixture to obtain 8.7 g of a mixture of 7-methylamino 5ξ-phenyl-5ξ-hydroxy-6,7,8,9-tetrahydro [5H] benzocycloheptene isomers which was used as is for the next step.

STEP B: 7-methylamino-9-phenyl-6,7-dihydro [5H] benzoycycloheptene hydrochloride 9.2 ml of 18 N sulfuric acid were added to a refluxing solution of 4.62 g of the product of Step A in 90 ml of dioxane and the mixture was refluxed for 15 minutes and was then cooled. The mixture was poured into iced water and was extracted with ethyl acetate. The organic phase was washed with aqueous sodium chloride solution, dried and evaporated to dryness. The residue was chromatographed over silica gel and was eluted with a 2-8-1 benzene-ethyl acetate-triethylamine mixture and then a 95-5-1 chloroform-methanol-triethylamine mixture to obtain 3.3 g of 7-methylamino-9-phenyl-6,7-dihydro [5H] benzocycloheptene.

The said product was dissolved in 500 ml of ether and an ether solution saturated with hydrogen chloride was added thereto. The mixture was filtered and the recovered precipitate was crystallized from isopropanol to obtain 2.3 g of the hydrochloride of the product melting at 244° C.

Analysis: $C_{18}H_{20}ClN$

| | | | | |
|---|---|---|---|---|
| Calculated: | %C 75.63 | %H 7.05 | %N 4.90 | %Cl 12.40 |
| Found: | 75.4 | 7.2 | 4.7 | 12.2 |

EXAMPLE 9

7-methylamino-5-phenyl-6,7,8,9-tetrahydro [5H] benzocycloheptene hydrochloride

A mixture of 2.47 g of 7-methylamino-9-phenyl-6,7-dihydro [5H] benzocycloheptene, 130 ml of ethanol, and 3.67 g of palladized carbon [10% pd(OH)$_2$] was maintained under a hydrogen atmosphere until absorption ceased and the mixture was filtered. The filtrate was evaporated to dryness and the residue was chromatographed over silica gel. Elution with a 4-6-1 benzene-ethyl acetate-triethylamine mixture yielded 1.82 g of 7-methylamino-5-phenyl-6,7,8,9-tetrahydro [5H] benzocycloheptene.

The said product was dissolved in 250 ml of ethyl ether and an ether solution saturated with hydrogen chloride was added thereto. The mixture was filtered and the recovered precipitate was crystallized from isopropanol to obtain 1.35 g of the hydrochloride of the said product melting at 265° C.

Analysis: $C_{18}H_{22}NCl$

| | | | | |
|---|---|---|---|---|
| Calculated: | %C 75.10 | %H 7.70 | %Cl 12.31 | %N 4.86 |
| Found: | 75.0 | 7.9 | 12.5 | 4.6 |

EXAMPLE 10

2- and 4-chloro-7-methylamino-6,7-dihydro [5H] benzocycloheptene hydrochloride

STEP A: 1- and 3-chloro-benzosuberone mixture 797 g of aluminum chloride were added over 20 minutes at 0° C to a solution of 400 g of benzosuberone in 1600 ml of 1,1,2,2-tetrachloroethane and then 166 ml of condensed chlorine were added thereto at 20° C over 5 ½ hours. The mixture was stirred at 20°-25° C over night and the mixture was then slowly added at 17° C to a mixture of water-ice-hydrochloric acid. The mixture was then extracted with methylene chloride and the extracts were washed successively with hydrochloric acid, water and sodium bicarbonate solution. The extracts were dried and evaporated to dryness and the residue was chromatographed over silica gel. Elution with benzene yielded 217 g of a mixture of 1- and 3-chloro-benzosuberone.

STEP B: 1- and 3-chloro-6-bromo-benzosuberone mixture

A mixture of 656 g of cuprous bromide and 3200 ml of ethyl acetate was refluxed for 45 minutes and then a solution of 328 g of the product of Step A in 1600 ml of chloroform was added at reflux over one hour. The mixture was refluxed for another 3 hours while adding another 151 g of cuprous bromide. The mixture was cooled and filtered and the filtrate was washed with a sodium chloride solution, was dried and evaporated to dryness to obtain 465 g of a raw mixture of 1- and 3-chloro-6-bromo-benzosuberone which was used as is for the next step.

STEP C: 1- and 3-chloro-8,9-dihydro [5H] benzocycloheptene -5-one mixture 459 g of lithium carbonate and 459 g of lithium bromide were added to a solution of 465 g of the product of Step B in 5 liters of dimethylformamide and the mixture was heated to 110° C for 2 ½ hours and was then cooled. The mixture was filtered and the filtrate was diluted with methylene chloride. The solution was washed with an aqueous sodium chloride solution, was dried and evaporated to dryness to obtain 397 g of a mixture of 1- and 3-chloro-8,9-dihydro [5H] benzocycloheptene-5-one.

STEP D: 1- and 3-chloro-5-oxo-7-methylamino-6,7,8,9-tetrahydro [5H] benzocycloheptene mixture A mixture of 100 g of the product of Step C, 500 ml of ethanol and 200 ml of a ethanol solution saturated with monomethylamine was stirred for 2 hours and was then evaporated to dryness. The residue was dissolved in a liter of ethyl acetate and the solution was extracted with 1N hydrochloric acid. The aqueous phase was made alkaline with sodium hydroxide and was extracted with ethyl acetate. The organic phase was washed with aqueous sodium chloride solution, was dried and evaporated to dryness to obtain 67.2 g of a 1- and 3-chloro-5-oxo-7-methylamino-6,7,8,9-tetrahydro [5H] benzocycloheptene in the form of a raw oil which was used as is for the next step.

STEP E: 1- and 3-chloro-5-hydroxy-7-methylamino-6,7,8,9-tetrahydro [5H] benzocycloheptene mixture A solution of 67.2 g of sodium borohydride in 800 ml of water was added to a solution of 67.2 g of the product of Step D in 2 liters of ethanol and the mixture was stirred for 4 hours at 20° C. The mixture was decanted and the organic phase was concentrated to 1000 ml and was extracted with ethyl acetate. The extracts were evaporated to dryness and the residue was chromatographed over silica gel and was eluted with an 8-1-1 ethyl acetate-methanol-triethylamine to obtain 41.5 g of a mixture of 1- and 3-chloro-5-hydroxy-7-methylamino-6,7,8,9-tetrahydro [5H] benzocycloheptene.

STEP F: 2- and 4-chloro-7-methylamino-6,7-dihydro [5H] benzocycloheptene hydrochloride mixture A mixture of the product of Step E and 800 ml of 2 N hydrochloric acid was refluxed for 24 hours and the mixture was cooled and was washed with ethyl acetate. The mixture was made alkaline and was extracted with ethyl acetate. The organic phase was washed with water, dried and concentrated to dryness and the residue was chromatographed over silica gel. Elution with an 8-2-1 ethyl acetate-methanol-triethylamine mixture yielded 14.1 g of a mixture of 2- and 4-chloro-7-methylamino-6,7-dihydro [5H] benzocycloheptene. The 2 isomers were separated by chromatography over silica gel and elution with a 95-5-1 ethyl acetate-methanol-methylamine mixture to obtain 8.7 g of the 4-chloro isomer and 2.5 g of the 2-chloro isomer.

The hydrochlorides of the two isomers were formed in ether solution saturated with hydrogen chloride to obtain 1.5 g of the 2-chloro isomer hydrochloride melting at 195° C and 9.6 g of the 4-chloro isomer hydrochloride melting at 225° C.

Analysis: $C_{12}H_{14}ClN$ (2 chloro isomer)

| | %C | %H | %N | %Cl |
|---|---|---|---|---|
| Calculated: | 59.03 | 6.19 | 5.74 | 29.04 |
| Found: | 59.1 | 6.4 | 5.7 | 29.2 |

EXAMPLE 11

4-chloro-7-methylamino-6,7-dihydro [5H] benzocyclopheptene hydrochloride

Using the procedure of Step A of Example 10, the chlorination was effected at 0° C to obtain 1-chloro-5-hydroxy-7-methylamino-6,7,8,9-tetrahydro [5H] benzocycloheptene. 14 g of the said product were dissolved in 280 ml of hexamethylphosphotriamide and the solution was heated to 220° C for 50 minutes and was then concentrated to 50 ml. The solution was cooled and was then poured into 500 ml of iced water. The pH of the mixture was adjusted to 10 by addition of concentrated ammonium hydroxide and was extracted with ethyl acetate. The organic extracts were washed with water, dried and concentrated to dryness and the residue was chromatographed over silica gel. Elution with a 95-5-10 ethyl acetate-methanol-triethylamine mixture yielded 2.2 g of 4-chloro-7-methylamino-6,7-dihydro [5H] benzocycloheptene.

2.19 g of the said product were dissolved in 260 ml of ethyl ether and 2 ml of ethyl ether saturated with hydrogen chloride were added thereto. The mixture was vacuum filtered and the recovered precipitate was crystallized from a methanol-ethyl acetate mixture to obtain 2.1 g of the hydrochloride of the said product melting at 228° C.

Analysis: $C_{12}H_{15}Cl_2N$

| | %C | %H | %N | %Cl |
|---|---|---|---|---|
| Calculated: | 59.02 | 6.19 | 5.73 | 29.04 |
| Found: | 58.9 | 6.3 | 5.7 | 28.7 |

EXAMPLE 12

7-ethylamino-6,7-dihydro [5H] benzocycloheptene hydrochloride

STEP A: 7-ethylamino-5-oxo-6,7,8,9-tetrahydro [5H] benzocycloheptene hydrochloride 20 ml of an ethanol solution containing 13% of ethylamine were added to a solution of 4.74 g of 5-oxo-8,9-dihydro [5H] benzocycloheptene in 20 ml of ethanol and the solution was stirred for 30 minutes at 20° C and was then evaporated to dryness. The residue was dissolved in methanol and a solution of methanol saturated with hydrochloric acid was added thereto. The mixture was evaporated to dryness and the residue was dissolved in acetone. The crystals formed were recovered by vacuum filtration to obtain 5.2 g of 7-ethylamino-5-oxo-6,7,8,9-tetrahydro [5H] benzocycloheptene hydrochloride melting at 212° C.

Analysis: $C_{13}H_{18}ClNO$

| | %C | %H | %Cl | %N |
|---|---|---|---|---|
| Calculated: | 65.12 | 7.57 | 14.79 | 5.84 |
| Found: | 65.2 | 7.8 | 15.1 | 5.8 |

STEP B: 7-ethylamino-5ξ-hydroxy-6,7,8,9-tetrahydro [5H] benzocycloheptene 1 g of sodium borohydride was slowly added to a solution of 0.96 g of the product of Step A in 10 ml of ethanol and 2 ml of 2 N sodium hydroxide solution and the mixture was stirred for 30 minutes at 20° C. 30 ml of water were added to the mixture and the ethanol was evaporated. The mixture was iced and extracted with methylene chloride. The organic phase was washed with water, dried and evaporated to dryness. The residue was taken up in isopropyl ether and the crystals formed were recovered by vacuum filtration to obtain 0.5 g of the 5β-OH isomer of 7-ethylamino-5-hydroxy-6,7,8,9-tetrahydro [5H] benzocycloheptene melting at 131° C and 0.4 g of the 5α-OH isomer in amorphous form were recovered from the mother liquor.

STEP C: 7-ethylamino-6,7-dihydro [5H] benzocycloheptene hydrochloride

A solution of 2.3 g of 7-ethylamino-5α-hydroxy-6,7,8,9-tetrahydro [5H] benzocycloheptane in 46 ml of dioxane was heated to reflux and 4.6 ml of 18 N sulfuric acid were added thereto. The mixture was refluxed for 30 minutes and was concentrated to 15 ml and then cooled. 100 ml of ice water and then concentrated ammonium hydroxide were added thereto and the mixture was extracted with methylene chloride. The organic extracts were washed with water, dried and evaporated to dryness to obtain 1.85 g of 7-ethylamino-6,7-dihydro [5H] benzocycloheptene.

The said product was dissolved in 5 ml of ethyl acetate saturated with hydrogen chloride and the mixture was vacuum filtered. The product was crystallized from methanol-ethyl acetate mixture to obtain 1.7 g of the hydrochloride of the said product melting at 180° C.

Analysis: $C_{13}H_{18}ClN$

| | | | | |
|---|---|---|---|---|
| Calculated: | %C 69.78 | %H 8.11 | %Cl 15.85 | %N 6.26 |
| Found: | 69.8 | 8.3 | 15.9 | 6.2 |

Treatment of the 5β-OH isomer under the same conditions led to the same product melting at 180° C.

EXAMPLE 13

7-(4-methylpiperazin-1-yl)-6,7,-dihydro [5H] benzocycloheptene difumarate

STEP A:
7-(4-methylpiperazin-1-yl)-5-oxo-6,7,8,9-tetrahydro [5H] benzocycloheptene A solution of 8 g of N-methylpiperazine in 80 ml of ethanol was added over 5 minutes to a solution of 6.32 g of 5-oxo-8,9-dihydro [5H] benzocycloheptene in 40 ml of ethanol and the mixture was stirred for 4 hours at 20° C and was then evaporated to dryness. The residue was taken up in 0.5 N hydrochloric acid and the solution was washed with ethyl acetate and made alkaline with concentrated ammonium hydroxide. The mixture was extracted with methylene chloride and the extracts were dried and evaporated to dryness to obtain 8.8 g of 7-(4-methylpiperazin-1-yl)-5-oxo-6,7,8,9-tetrahydro [5H] benzocycloheptene.

STEP B:
7-(4-methylpiperazin-1-yl)-5ξ-hydroxy-6,7,8,9-tetrahydro [5H] benzocycloheptene 8.8 g of sodium borohydride were added over 20 minutes at 22°-26° C to a solution of 8.8 g of the product of Step A in 8.8 ml of ethanol and 8.8 ml of water and the mixture was stirred for 1 hour at 20° C. The ethanol was evaporated and the mixture was poured into water and was extracted with methylene chloride. The organic extracts were washed with water, dried and evaporated to dryness to obtain 9 g of a mixture of the isomers of raw 7-(4-methylpiperazin-1-yl)-5-hydroxy-6,7,8,9-tetrahydro [5H] benzocycloheptene which was used as is for the next step.

STEP C: 7-(4-methylpiperazin-1-yl(-6,7-dihydro [5H] benzocycloheptene difumarate 18 ml of 18 N sulfuric acid were added to a refluxing solution of 9 g of the product of Step B in 180 ml of dioxane and the mixture was refluxed for 30 minutes and then was concentrated and cooled to 20° C. 100 ml of ice-water were added thereto and the mixture was extracted with ethyl acetate. The aqueous phase was made alkaline with concentrated ammonium hydroxide and was extracted with methylene chloride. The organic phase was dried and evaporated to dryness to obtain 6.2 g of 7-(4-methylpiperazin-1-yl)-6,7-dihydro [5H] benzocycloheptene.

The said product was dissolved in 80 ml of ethanol and 6 g of fumaric acid were added thereto. The mixture was allowed to crystallize for a few hours and was then vacuum filtered. The recovered crystals were crystallized from methanol to obtain 9 g of the difumarate of the said product melting at 210° C.

Analysis: $C_{24}H_{30}N_2O_8$

| | | | |
|---|---|---|---|
| Calculated: | %C 60.75 | %H 6.37 | %N 5.90 |
| Found: | 60.6 | 6.4 | 5.7 |

EXAMPLE 14

7-allylamino-6,7-dihydro [5H] benzocycloheptene hydrochloride

STEP A: 7-allylamino-5-oxo-6,7,8,9-tetrahydro [5H] benzocycloheptene hydrochloride A solution of 4.6 g of allylamine in 46 ml of ethanol was added to a solution of 6.33 g of 5-oxo-8,9-dihydro [5H] benzocycloheptene in 30 ml of ethanol and the mixture was stirred at 20° C for 1 hour and was evaporated to dryness. The residual oil was taken up in 30 ml of ethyl acetate and an ethyl acetate solution saturated with hydrogen chloride was added thereto. The mixture was vacuum filtered to obtain 7.3 g of 7-allylamino-5-oxo-6,7,8,9-tetrahydro [5H] benzocycloheptene hydrochloride melting at 170° C.

STEP B: 7-allylamino-5ξ-hydroxy-6,7,8,9-tetrahydro [5H] benzocycloheptene 7.3 g of sodium borohydride was added over 30 minutes at 15° C to a solution of 7.3 g of the product of Step A in 7 3 ml of ethanol and 7.3 ml of water and the mixture was stirred for an hour at 20° C. The mixture was made alkaline with concentrated sodium hydroxide and the ethanol was evaporated. Water was added thereto and the mixture was extracted with methylene chloride. The organic phase was washed with water, dried and evaporated to dryness to obtain 6.2 g of 7-allylamino-5ξ-hydroxy-6,7,8,9-tetrahydro [5H] benzocycloheptene.

STEP C: 7-allylamino-6,7-dihydro [5H] benzocycloheptene hydrochloride 12.4 ml of 18 N sulfuric acid were added to a refluxing solution of 6.2 g of 7-allylamino-5-ξ-hydroxy-6,7,8,9-tetrahydro [5H] benzocycloheptene in 124 ml of dioxane and the mixture was refluxed for 30 minutes and was cooled. The mixture was concentrated to 40 ml and 100 ml of ice water were added. The aqueous phase was washed with ethyl acetate and made alkaline with concentrated ammonium hydroxide. The mixture was extracted with methylene chloride and the organic phase was washed with water, dried and evaporated to dryness to obtain 4.5 g of 7-allylamino-6,7-dihydro [5H] benzocycloheptene.

The said product was dissolved in 5 ml of ethyl acetate and a solution of ethyl acetate saturated with hydrochloric acid was added at 15°-20° C. The solvent was evaporated and the residue was crystallized from isopropanol. The product was then crystallized from methyl ethyl ketone to obtain 3.6 g of the hydrochloride of the product melting at 148° C.

Analysis: $C_{14}H_{18}ClN$

| | | | | |
|---|---|---|---|---|
| Calculated: | %C 71.32 | %H 7.69 | %Cl 15.04 | %N 5.94 |
| Found: | 71.2 | 7.9 | 14.8 | 5.9 |

EXAMPLE 15

Di-[7-(pyrrolidin-1-yl)-6,7-dihydro [5H] benzocycloheptene] fumarate

STEP A: 5-oxo-7-(pyrrolidin-1-yl)-6,7,8,9-tetrahydro [5H] benzocycloheptene

A solution of 7.1 g of pyrrolidine in 30 ml of ethanol was added to a solution of 7.9 g of 5-oxo-6,7-dihydro [5H] benzocycloheptene in 30 ml of ethanol and the mixture was stirred at room temperature for 30 minutes and was evaporated to dryness to obtain 11.5 g of 5-oxo-7-(Pyrrolidin-1-yl)-6,7,8,9-tetrahydro [5H] benzocycloheptene.

STEP B:
5ξ-hydroxy-7-(pyrrolidin-1-yl)-6,7,8,9-tetrahydro [5H] benzocycloheptene 5.75 g of sodium borohydride were slowly added to a solution of 11.5 g of the product of Step A in 11 5 ml of ethanol and 11.5 ml of water cooled to 10° C and the mixture was stirred for an hour at 20° C. The ethanol was evaporated and 100 ml of water were added. The mixture was extracted with methylene chloride and the organic phase was washed with water, dried and evaporated to dryness to obtain 11.35 g of 5ξ-hydroxy-7-(pyrrolidin-1-yl)-6,7,8,9-tetrahydro [5H] benzocycloheptene.

STEP C: di-[7-(pyrrolidin-1-yl)-6,7-dihydro [5H] benzocycloheptene] fumarate

A mixture of 5 g of the product of Step B and 5 g of anhydrous potassium acid sulfate was heated for 5 minutes at 220° C and the mixture was cooled to 25° C and was taken up in water. The aqueous phase was washed with ether and made alkaline with concentrated ammonium hydroxide. The mixture was extracted with methylene chloride and the organic phase was dried and evaporated to dryness to obtain 3.3 g of raw di-[7-(pyrrolidin-1-yl)-6,7-dihydro [5H] benzocycloheptene].

The 3.3 g of raw product were dissolved in 25 ml of isopropanol and 870 mg of fumaric acid were added thereto. The mixture was heated until dissolution occurred and was then held at 20° C for 2 hours. The mixture was vacuum filtered and the precipitate was washed with isopropanol and then with ether to obtain 1.75 g of the fumarate of the said product melting at 190° C, then 200° C. Crystallization from methanol did not change the melting point.

| Analysis: $C_{30}H_{38}N_2 \cdot C_4H_4O_4$ | | | |
|---|---|---|---|
| Calculated: | %C 75.24 | %H 7.80 | %N 5.16 |
| Found: | 75.0 | 8.2 | 5.1 |

EXAMPLE 16

2-chloro-7-methylamino-6,7-dihydro [5H] benzocycloheptene hydrochloride

STEP A: 3-chloro-5-oxo-8,9-dihydro [5H] benzocycloheptene

A mixture of 12 g of pyridinium perbromide in 10 ml of dimethylformamide was added over 10 minutes at 80° C to a solution of 7.1 g of 3-chloro-suberone [J.Chem., Soc. C., (1969), p. 2176] in 10.5 ml of dimethylformamide and the mixture was held at 80° C for 15 minutes. The solution was introduced at 120° C over 20 minutes to a mixture of 7 ml of dimethylformamide, 12.4 g lithium carbonate and 10 g of lithium bromide and the mixture was stirred at 120° C for 2 ⅓ hours and was then cooled to 50° C. The mixture was then poured into 60 ml of water, 120 g of ice and 23 ml of hydrochloric acid and the mixture was extracted with ether. The ether extracts were washed with water, dried, treated with activated carbon, filtered and evaporated to dryness to obtain 7 g of raw 3-chloro-5-oxo-8,9-dihydro [5H] benzocycloheptene which was used as is for the next step. The product when purified by chromatography over silica gel, elution with an 8-2 cyclohexane-ethyl acetate mixture and crystallization from ether melted at 55° C.

STEP B:
3-chloro-5-oxo-7-methylamino-6,7,8,9-tetrahydo [5H] benzocycloheptene hydrochloride A solution of 9 g of the product of Step A in 50 ml of ethanol was added at 20° C to 60 ml of an ethanol solution of 5 N monomethylamine and the mixture was stirred for an hour and then evaporated to dryness. The residue was taken up in N hydrochloric acid and the solution was washed with ether and was cooled to 10° C. The mixture was made alkaline with concentrated ammonium hydroxide and was extracted with ether. The ether extracts were washed with water, dried, treated with activated carbon and filtered. The filtrate was evaporated to dryness to obtain 7.6 g of product which was dissolved in 5 ml of methanol. The mixture was cooled to 10° C and a solution of ethyl acetate saturated with hydrogen chloride was added thereto. The mixture was vacuum filtered to obtain 4.6 g of 3-chloro-5-oxo-7-methylamino-6,7,8,9-tetrahydro [5H] benzocycloheptene hydrochloride melting at 218° C.

STEP C:
3-chloro-5ξ-hydroxy-7-methylamino-6,7,8,9-tetrahydro [5H] benzocycloheptene Sodium hydroxide solution was added to suspension of 4.6 g of the product of Step B in 100 ml of water cooled to 10° C and the mixture was extracted with methylene chloride. The extracts were dried and evaporated to dryness and the 4 g of oily residue were dissolved in 40 ml of ethanol and 4 ml of water. 2 g of sodium borohydride were added to the mixture at 20° C and the mixture was stirred for an hour. The mixture was evaporated to dryness and the residue was taken up in methylene chloride. The solution was washed with water, dried and evaporated to dryness. The residue was washed with isopropyl ether to obtain 3.7 g of 3-chloro-5ξ-hydroxy-7-methylamino-6,7,8,9-tetrahydro [5H] benzocycloheptene melting at 90° C.

STEP D: 2-chloro-7-methylamino-6,7-dihydro [5H] benzocycloheptene hydrochloride 7.4 ml of concentrated sulfuric acid were added to a refluxing solution of 3.7 g of 3-chloro-5ξ-hydroxy-7-methylamino-6,7,8,9-tetrahydro [5H] benzocycloheptene in 37 ml of dioxane and the mixture was refluxed for 20 minutes and then was cooled to 20° C. 50 ml of water were added to the reaction mixture which was then made alkaline with sodium hydroxide. The mixture was extracted with methylene chloride and the organic extracts were washed with water, dried and evaporated to dryness. The resulting 3.5 g of product were dissolved in 5 ml of ethyl acetate and a solution of ethyl acetate saturated with hydrogen chloride was added thereto at 10° C. The mixture was vacuum filtered to obtain 3.3 g of 2-chloro-7-methylamino-6,7-dihydro [5H] benzocycloheptene hydrochloride melting at 195° C which was identical to the product of Example 10.

EXAMPLE 17

2-chloro-7-dimethylamino-6,7-dihydro [5H] benzocycloheptene fumarate 7.7 ml of an aqueous solution of 40% formaldehyde and then 4.5 g of sodium cyanoborohydride were added to a mixture of 4.7 g of 2-chloro-7-methylamino-6,7-dihydro [5H] benzocycloheptene hydrochloride in 47 ml of acetonitrile and the mixture was stirred for 15 minutes at room temperature. Acetic acid was added to the reaction mixture until the pH was 7 and the mixture was stirred at room temperature for 45 minutes. The mixture was evaporated to dryness under reduced pressure to obtain 2.6 g of 2-chloro-7-dimethylamino-6,7-dihydro [5H] benzocycloheptene in the form of an oil. Addition of a solution of fumaric acid in methanol yielded 3.3 g of the fumarate of the said product melting at 160° C.

Analysis: $C_{13}H_{16}ClN \cdot C_4H_4O_4$; molecular weight = 337.795

| | %C | %H | %N | %Cl |
|---|---|---|---|---|
| Calculated: | 60.44 | 5.97 | 4.15 | 10.50 |
| Found: | 60.2 | 6.0 | 4.1 | 10.7 |

EXAMPLE 18

Tablets were prepared from 25 mg of 7-dimethylamino-6,7-dihydro [5H] benzocycloheptene hydrochloride, or from 25 mg of 7-dimethylamino-5-phenyl-6,7,8,9-tetrahydro [5H] benzocycloheptene hydrochloride, or from 25 mg of 7-methylamino-6,7-dihydro [5H] benzocycloheptene hydrochloride or from 25 mg of 2-chloro-7-methylamino-6,7-dihydro [5H] benzocycloheptene hydrochloride and sufficient excipient of lactose, starch, talc and magnesium stearate for a final tablet of 200 mg.

PHARMACOLOGICAL DATA

A. Potentiation of effects of monoamine oxidase inhibitor

The administration of a monoamine oxidase inhibitor to mice induces a hyperactive movement of the animals which is able to be potentiated by an antidepressant. Using the procedure of Carlsson et al [Brain Research, Vol. 12 (1969), p. 456], a dose of 100 mg/kg of nialamide was intraperitoneally administered to mice 30 minutes before the intraperitoneal administration of the tested product and the values of actimetric measurements were recorded every 30 minutes for 6 hours. Potentiation of the effects of nialamide for the tested product was expressed in increasing number of + signs for a determined dose in mg/kg. The results are reported in Table I.

TABLE I

| Product of Example | | Potentiation of nialamide in mg/kg |
|---|---|---|
| 1 | | + + 20 |
| 2 | | + 1-5 |
| | | + + + 20 |
| 5 | | + 1 |
| | | + + + 20 |
| 6 | | + + 5 |
| | | + + + 20 |
| . | | + 5 |
| | | + + 20 |
| 10 | (2-chloro derivative) | + + + 1 |
| | | + + + 5 |

TABLE I-continued

| Product of Example | Potentiation of nialamide in mg/kg |
|---|---|
| 11 | + 5 |
| | + + + 20 |
| 13 | + + 20 |
| 14 | + + 20 |

The results of Table I show that the compounds of the invention potentiate in an important manner the effects of nialamide.

B. Potentiation of effects of 5-HTP

The administration of 5-hydroxytryptophane (5-HTP) to mice pretreated with an antidepressant induces in the animals a particular behavior, namely the appearance of trembling. The tested products were administered intraperitoneally at increasing doses one hour before the intraperitoneal administration of 5-HTP at an dose of 200 mg/kg. The symptoms were observed every 15 minutes for an hour to determine the miminal active dose (MAD) of the test product and the results are reported in Table II.

TABLE II

| Product of Example | (MAD) in mg/kg |
|---|---|
| 1 | 20 |
| 5 | 10 |
| 6 | 5 |
| 9 | 20 |
| 10 (2-chloro-derivative) | 10 |
| 11 | 20 |
| 12 | 20 |
| 13 | 50 |
| 14 | 50 |

The results of Table II show that the products of the invention potentiate in an important manner the effects of 5-HTP.

C. Potentiation of effects of L-dopa.

The administration of L-dopa to mice pretreated 18 hours previously with iproniazide produced certain number of symptoms; muscular hypertonically, hyperactivity, agitation, crying, aggressiveness, salivation and exophthalmy. The intensity of these effects is potentiated by administration of an antidepressant one hour before the administration of L-dopa. Male mices received intraperitoneally 75 mg/kg of iproniazide 18 hours before the start of the test and the tested product was intraperitoneally administered in aqueous solution in increasing doses. One hour later, L-dopa was intraperitoneally administered at a dose of 100 mg/kg and the different symptoms were observed 15 and 30 minutes later. They were evaluated on a scale of 0 to 3 for each animal and the totals for each dose were determined. The $ED_{50}$ dose which potentiates by 50% the L-dopa effects was determined and is reported in Table III.

TABLE III

| Product of Example | | $ED_{50}$ in mg/kg |
|---|---|---|
| 1 | | <5 |
| 2 | | 5 |
| 3 | | 2 |
| 5 | | 2 |
| 6 | | 10 |
| 7 | | 10 |
| 8 | | 5 |
| 9 | | 5 |
| 10 | (2-chloro-derivative) | <5 |
| 11 | | 20 |

TABLE III-continued

| Product of Example | ED$_{50}$ in mg/kg |
|---|---|
| 12 | 10 |
| 13 | 20 |
| 14 | 20 |

The results of Table III show that the compounds of the invention potentiate in an important manner the effects of L-dopa.

D. Acute toxicity

The LD$_{50}$ dose which kills 50% of mice after intraperitoneal administration of the tested compounds was determined 48 hours later and the results are reported in Table IV.

TABLE IV

| Product of Example | | LD$_{50}$ in mg/kg |
|---|---|---|
| 1 | | 75 |
| 2 | | 100 |
| 3 | | 100 |
| 4 | | 50 |
| 5 | | 50 |
| 6 | | 75 |
| 7 | | 100 |
| 8 | | 50 |
| 9 | | 50 |
| 10 | (2-chloro-derivative) | 75 |
| 11 | | 75 |
| 12 | | 75 |
| 13 | | 250 |
| 14 | | 150 |

BIOCHEMICAL STUDY

A. Inhibition of Serotonine uptake in vitro

The inhibition of serotonine (5HT) uptake was measured in impure synaptosomes prepared from the entire brain of a female rat 19 to 21 days old using the technique of Kannengiesser et al [Biochemical Pharmacology, Vol. 22, (1973) p. 73]. Diverse concentrations of the products were placed in an incubator with the preparation at 37° C for 5 minutes in the presence of 14 C-5HT at a concentration of $10^{-7}$M. The 50% inhibiting concentration (IC$_{50}$), dose which inhibits by 50% the uptake of 14 C-5HT in the synaptosomes was determined graphically and the IC$_{50}$ dose for the compounds is reported in Table V.

B. Inhibition of Serotonine uptake in vivo.

The tested products were intraperitoneally administered to groups of female rats 19 to 21 days old at doses of 5 to 20 mg/kg. After 30 minutes, the brain was removed and synaptosomes were prepared and placed in an incubator in the presence of 14 C-5HT as indicated in the previous test. The relative power of the products to inhibit the uptake of 14 C-5HT was estimated with respect to a test effected with animals which did not receive the tested product and the activity was expressed in increasing number of + signs. The results are reported in Table V.

TABLE V

| Product of Example | Test in vitro I.C. 50 (M) | Test in vivo |
|---|---|---|
| 1 | 5.1 × 10$^{-7}$ | ++ |
| 5 | 1.5 × 10$^{-7}$ | +++ |
| 6 | 1.9 × 10$^{-6}$ | ++ |
| 10 (2-chloro derivative) | 3.5 × 10$^{-7}$ | +++ |
| 11 | 4.0 × 10$^{-7}$ | + |

The results of Table V show that the compounds of the invention possess very interesting serotoninergic properties.

Various modifications of the products and methods of the invention may be made without departing from the spirit or scope thereof and it should be understood that the invention is intended to be limited only as defined in the appended claims.

We claim:

1. A compound selected from the group consisting of 7-amino-benzocycloheptenes of the formula

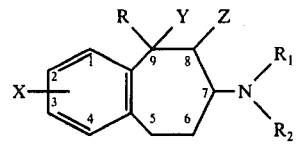

wherein X is selected from the group consisting of hydrogen, chlorine, bromine and iodine in the 2- or 4-position when a halogen, Y and Z together form a double bond, R is selected from the group consisting of hydrogen, alkyl of 1 to 5 carbon atoms, phenyl and phenyl substituted with a fluorine, chlorine, methyl or methoxy, R$_1$ is selected from the group consisting of hydrogen, alkyl of 1 to 5 carbon atoms and alkenyl of 2 to 5 carbon atoms and R$_2$ is selected from the group consisting of alkyl of 1 to 5 carbon atoms and alkenyl of 2 to 5 carbon atoms and R$_1$ and R$_2$ taken together with the nitrogen atom to which they are attached form a member selected from the group consisting of pyrrolidino, N-ethyl-piperidino, morpholino, piperazinyl, N-methyl-piperazinyl, N-ethyl-piperazinyl, N-propyl-piperazinyl and N-butyl-piperazinyl and their non-toxic, pharmaceutically acid addition salts.

2. A compound of claim 1 wherein X is selected from the group consisting of hydrogen and chlorine, R is selected from the group consisting of hydrogen, methyl and phenyl, R$_1$ is selected from the group consisting of hydrogen, methyl, ethyl, propyl and allyl, R$_2$ is selected from the group consisting of methyl, ethyl, propyl and allyl and R$_1$ and R$_2$ taken with the nitrogen atom form a heterocycle selected from the group consisting of pyrrolidino, piperidino, morpholino, piperazinyl and N-methyl piperazinyl.

3. A compound of claim 1 wherein R is selected from the group consisting of hydrogen and phenyl, R$_1$ is selected from the group consisting of hydrogen, methyl ethyl and allyl, R$_2$ is selected from the group consisting of methyl, ethyl and allyl and R$_1$ and R$_2$ together with the nitrogen atom form a heterocycle selected from the group consisting of pyrrolidino and N-methyl piperazinyl.

4. A compound of claim 1 wherein R$_1$ is selected from the group consisting of hydrogen and methyl and R$_2$ is selected from the group consisting of methyl, ethyl and allyl.

5. A compound of claim 1 selected from the group consisting of 7-dimethylamino-6,7-dihydro [5H] benzocycloheptene and its non-toxic, pharmaceutically acceptable acid addition salts.

6. A compound of claim 1 selected from the group consisting of 7-methylamino-6,7-dihydro [5H] benzocycloheptene and its non-toxic, pharmaceutically acceptable acid addition salts.

7. A compound of claim 1 selected from the group consisting of 2-chloro-7-methylamino-6,7-dihydro [5H]

benzocycloheptene and its non-toxic, pharmaceutically acceptable acid addition salts.

8. A compound of claim 1 which is di [7-(pyrrolidino)-1-yl)6,7-dihydro [5H] benzocycloheptene fumarate.

9. A compound selected from the group consisting of A and B isomers of 7-dimethylamino-5-phenyl-6,7,8,9-tetrahydro [5H] benzocycloheptene and its non-toxic, pharmaceutically acceptable acid addition salts.

10. A compound of claim 6 selected from the group consisting of the enantiomorphs of 7-methylamino-6,7-dihydro [5H] benzocycloheptene.

11. A compound of claim 1 wherein R is selected from the group consisting of phenyl and phenyl substituted with a fluorine, chlorine, methyl or methoxy.

12. An antidepressive composition comprising an antidepressively effective amount of at least one compound selected from the group consisting of 7-aminobenzocycloheptenes of the formula

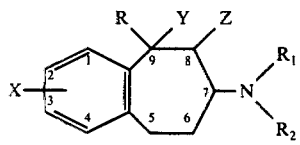

wherein X is selected from the group consisting of hydrogen, chlorine, bromine and iodine in the 2- or 4-position when a halogen, Y and Z are hydrogen or together form a double bond, R is selected from the group consisting of hydrogen, alkyl of 1 to 5 carbon atoms, phenyl and phenyl substituted with a fluorine, chlorine, methyl or methoxy, $R_1$ is selected from the group consisting of hydrogen, alkyl of 1 to 5 carbon atoms and alkenyl of 2 to 5 carbon atoms and $R_2$ is selected from the group consisting of alkyl of 1 to 5 carbon atoms and alkenyl of 2 to 5 carbon atoms and $R_1$ and $R_2$ taken together with the nitrogen atom to which they are attached form a member selected from the group consisting of pyrrolidino, N-ethyl-piperidino, morpholino, piperazinyl, N-methyl-piperazinyl, N-ethyl-piperazinyl, N-propyl-piperazinyl and N-butyl-piperazinyl and their non-toxic, pharmaceutically acid addition salts and an inert pharmaceutical carrier.

13. A composition of claim 12 wherein X is selected from the group consisting of hydrogen and chlorine, R is selected from the group consisting of hydrogen, methyl and phenyl, $R_1$ is selected from the group consisting of hydrogen, methyl, ethyl, propyl and allyl, $R_2$ is selected from the group consisting of methyl, ethyl, propyl and allyl and $R_1$ and $R_2$ taken with the nitrogen atom form a heterocycle selected from the group consisting of pyrrolidino, piperidino, morpholino, piperazinyl and N-methyl piperazinyl.

14. A composition of claim 12 wherein R is selected from the group consisting of hydrogen and phenyl, $R_1$ is selected from the group consisting of hydrogen and phenyl, $R_1$ is selected from the group consisting of hydrogen, methyl, ethyl and allyl, $R_2$ is selected from the group consisting of methyl, ethyl and allyl and $R_1$ and $R_2$ together with the nitrogen atom form a heterocycle selected from the group consisting of pyrrolidino and N-methyl piperazinyl.

15. A composition of claim 12 wherein $R_1$ is hydrogen or methyl and $R_2$ is methyl, ethyl or allyl.

16. A method of relieving depression in warm-blooded animals comprising administering to warm-blooded animals in antidepressive effective amount of at least one compound selected from the group consisting of 7-aminobenzocycloheptenes of the formula

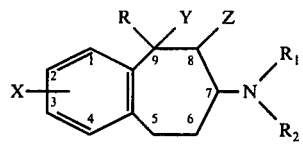

wherein X is selected from the group consisting of hydrogen, chlorine, bromine and iodine in the 2- or 4-position when a halogen, Y and Z are hydrogen or together form a double bond, R is selected from the group consisting of hydrogen, alkyl of 1 to 5 carbon atoms, phenyl and phenyl substituted with a fluorine, chlorine, methyl or methoxy, $R_1$ is selected from the group consisting of hydrogen, alkyl of 1 to 5 carbon atoms and alkenyl of 2 to 5 carbon atoms and $R_2$ is selected from the group consisting of alkyl of 1 to 5 carbon atoms and alkenyl of 2 to 5 carbon atoms and $R_1$ and $R_2$ taken together with the nitrogen atom to which they are attached form a member selected from the group consisting of pyrrolidino, N-ethyl-piperidino, morpholino, piperazinyl, N-methyl-piperazinyl, N-ethyl-piperazinyl, N-propyl-piperazinyl and N-butyl-piperazinyl and their non-toxic, pharmaceutically acid addition salts.

17. The method of claim 16 wherein X is selected from the group consisting of hydrogen and chlorine, R is selected from the group consisting of hydrogen, methyl and phenyl, $R_1$ is selected from the group consisting of hydrogen, methyl, ethyl, propyl and allyl, $R_2$ is selected from the group consisting of methyl, ethyl, propyl and allyl and $R_1$ and $R_2$ taken with the nitrogen atom form a heterocycle selected from the group consisting of pyrrolidino, piperidino, morpholino, piperazinyl and N-methyl piperazinyl.

18. The method of claim 16 wherein R is selected from the group consisting of hydrogen and phenyl, $R_1$ is selected from the group consisting of hydrogen, methyl, ethyl and allyl, $R_2$ is selected from the group consisting of methyl, ethyl and allyl and $R_1$ and $R_2$ together with the nitrogen atom form a heterocycle selected from the group consisting of pyrrolidine and N-methyl piperazinyl.

19. The method of claim 16 wherein $R_1$ is hydrogen or methyl and $R_2$ is methyl, ethyl or allyl.

* * * * *